United States Patent [19]

Goodkin

[11] 4,351,091
[45] Sep. 28, 1982

[54] METHOD OF PRESERVING CORPSES

[76] Inventor: Richard P. Goodkin, 336 Singletary La., Framingham, Mass. 01701

[21] Appl. No.: 170,958

[22] Filed: Jul. 21, 1980

[51] Int. Cl.³ .............................................. A01N 1/00
[52] U.S. Cl. ................................ 27/22 R; 250/492.1; 422/21; 422/40
[58] Field of Search ........................................... 27/22

[56] References Cited

U.S. PATENT DOCUMENTS

| | | | |
|---|---|---|---|
| 746,284 | 12/1903 | Karwowski | 27/22 |
| 3,494,723 | 2/1970 | Gray | 21/54 |
| 3,494,724 | 2/1970 | Gray | 21/54 |
| 3,638,709 | 2/1972 | Brown, Jr. et al. | 156/57 |

OTHER PUBLICATIONS

"Food Irradiation and Nutrition", by Brynjolfsson et al, The Professional Nutritionist, 1979.
"Microbiological Safety of Radappertized Beef", Anellis et al, Food Technology, May 1979.

*Primary Examiner*—John D. Yasko
*Attorney, Agent, or Firm*—Arthur W. Fisher

[57] ABSTRACT

A method of preserving anatomical specimens for long periods of time including the steps of encasing the specimen in an air-tight container, exchanging the atmospheric contents in the container with an inert gas, and irradiating the specimen.

13 Claims, 7 Drawing Figures

METHOD OF PRESERVING CORPSES

FIELD OF THE INVENTION

This invention relates to methods of preserving anatomical specimens and, more particularly, a method of preserving human corpses for long periods of time.

BACKGROUND OF THE INVENTION

When the human body dies, a number of processes are set into motion which contribute to the decomposition of the corpse.

Internally, the tissues of the body undergo a lysis or digestion after the initial stages of somatic death have occurred. Specifically, after the corpse has undergone algor mortis, liver mortis, and rigor mortis, the tissues of the body undergo a digestion or decomposition which is accelerated by the presence of putrefaction bacteria released from the intestine and the presence and feeding of other pathogenic microorganisms within the body.

Decomposition of the corpse is also enhanced or accelerated by the breakdown of autolytic and proteolytic enzymes in the tissues of the body which take place after death. Externally, the interaction and feeding of microorganisms and insects coupled with the oxidative reaction induced by the surrounding atmosphere further contribute to the decay of the corpse.

Today, the principal means used for preparation of corpses for burial is the embalming process wherein the blood in the corpse is removed and replaced with a chemical solution. For the most part, such corpses are subsequently buried in a casket where they are quickly subjected to the above mentioned decaying processes. The principal effect of the embalming process is to merely retard the decomposition of the body or, more particularly, the externally visible effects thereof for a relatively brief period of time; typically a few days. In some cases, much stronger solutions of preservatives are used to further delay the decaying process. However, these solutions cause chemical changes in the body tissues.

Other methods have been proposed and/or used for preserving corpses for more substantial periods of time. These include various chemical treatments such as bleaching, encasing of the corpse in air-tight containers, and cryogenic processes wherein the corpse is subjected to a deep freeze. For the most part, the chemical treatments which have been proposed, such as bleaching, are only a slight improvement over the traditional method of embalming in terms of delaying the decomposition of the corpse.

Encasement of the corpse in hermetically sealed containers has also been proposed. However, this process has not been coupled with any other steps to prevent or retard the decaying process, particularly, microbiological and chemical reaction processes which occur during decomposition.

Finally, cryogenics have been used for some time to prevent decomposition of the body. Although this method is relatively effective by comparison to the other methods of preserving bodies mentioned above, it is quite expensive and requires continuous effort to maintain the frozen environment in which the corpse is preserved.

Consequently, it is an object of this invention to provide a method of preparing corpses for storage and/or burial in which the body is preserved and protected from decomposition for substantial periods of time.

It is a further object of this invention to provide such a method of preserving bodies which is economical.

It is still a further object of this invention to provide a method of preserving bodies in which embalming or other manually administered chemical treatments are not required.

It is still another object of this invention to provide a method of preserving corpses in which the corpse may be continually viewed without deterioration or cosmetic change.

These and other objects shall become apparent from the following specifications.

SUMMARY

The present invention comprises a method of preserving corpses including steps of encasing the corpse in a container or casket preferably comprised of a clear plastic polymer, exchanging the atmosphere within the container with an inert gas to prevent oxidation, heating the corpse sufficiently to deactivate enzymatic breakdown, and irradiating the body to kill bacteria and microorganisms.

DESCRIPTION OF THE PREFERRED EMBODIMENT

Figure 1:
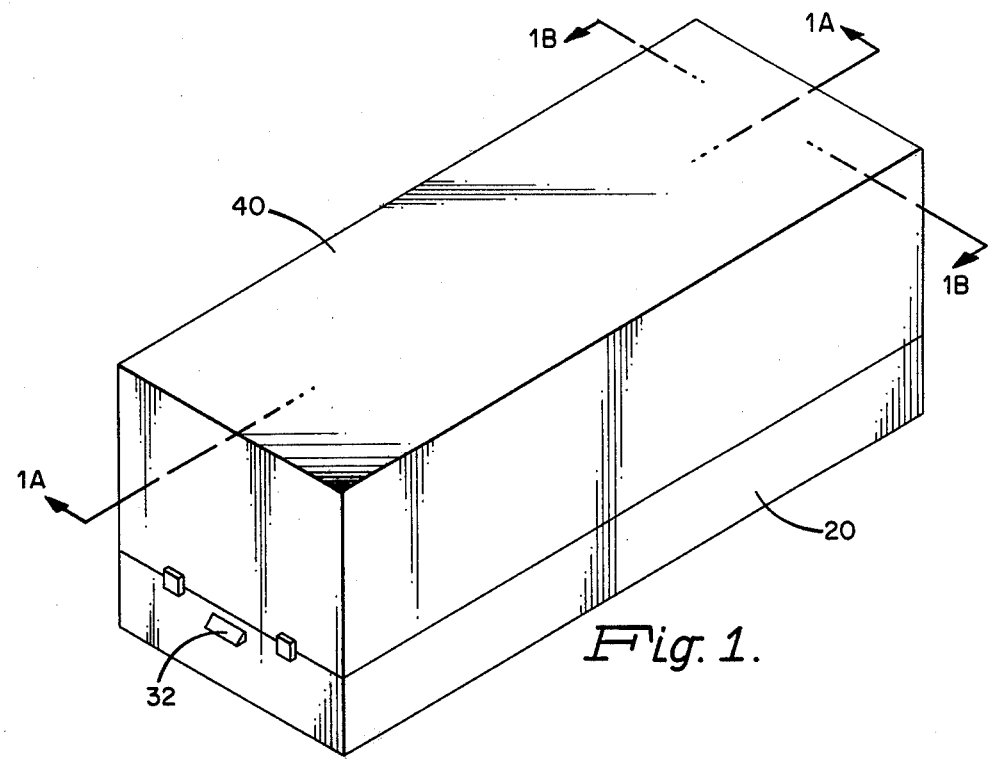
FIG. 1 is a perspective view of a container used in the present invention.
Figure 1A:
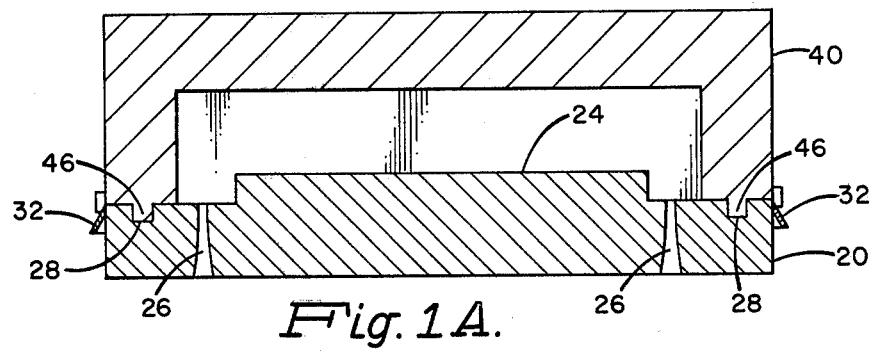
FIG. 1A is a side view of FIG. 1.
Figure 1B:
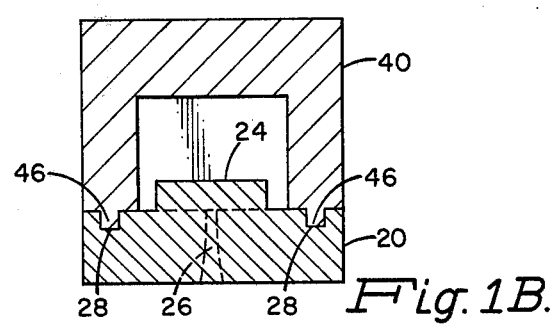
FIG. 1B is an end view of FIG. 1.

Referring to FIG. 1A, a container 10 for storing a corpse is depicted. The container 10 has a bottom portion 20 and a top portion 40 as shown in FIGS. 2A and 2B, and FIGS. 3A and 3B respectively and can be fabricated from any of a number of materials. The materials, however, must be capable of forming an air-tight seal and must be permeable with respect to the irradiation and heating processes described in greater detail below.

A material, such as a plastic polymer, is particularly suitable for such a container since it is readily adaptable for use as an air-tight container, is permeable with respect to the heating and irradiating processes described below, is inexpensive and is resistent to decay, discoloration, rust, and other biodegradation processes. Additionally, a transparent plastic, either clear or tinted, allows the corpse to be viewed for an indefinite period of time in a fixed state.

Figure 2A:
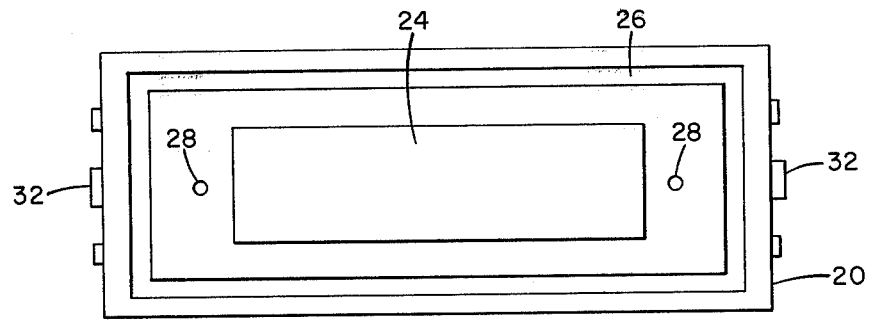
FIG. 2A is a top view of the bottom portion of the container shown in FIG. 1A.
Figure 2B:
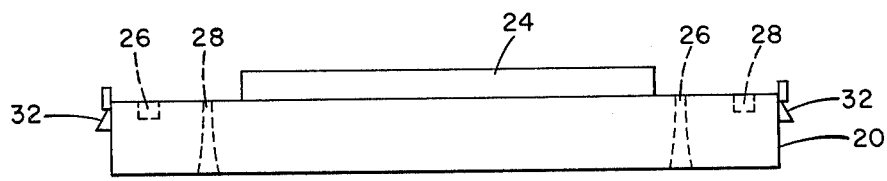
FIG. 2B is a side view of the bottom portion of the container shown in FIG. 2A.
Figure 3A:
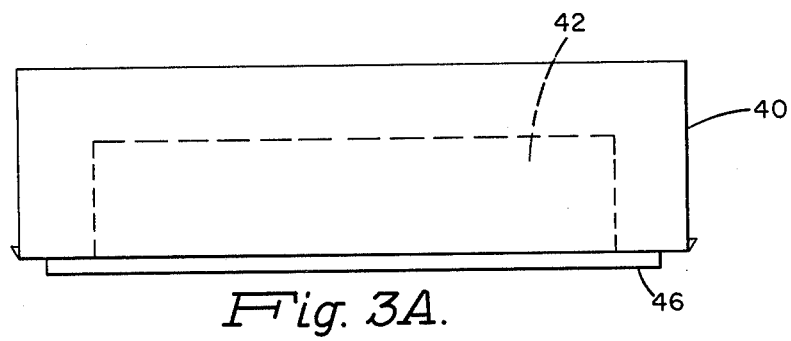
FIG. 3A is a side view of the top portion of the container shown in FIG. 1A.
Figure 3B:
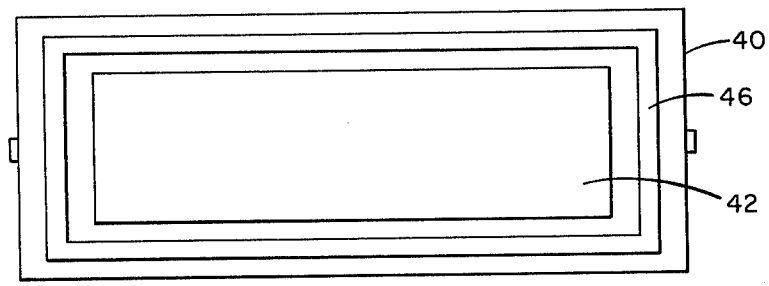
FIG. 3B is a bottom view of the top portion of the container shown in FIG. 3A.

Referring now to FIGS. 2A and 2B, the bottom portion of the container 10 is comprised of a base 22 having a raised portion or pedestal 24 extending therefrom on which the corpse is placed. The surface of the base 22 from which the pedestal extends, includes a cavity or channel 26 therein which extends around the perimeter of the pedestal 24.

The base 22 also includes two cylindrical cavities 28 extending therethrough. The extremity of the cavities 28 which end at the lower surface 30 of the base 22 may be tapered or threaded to receive a plug as will be described in more detail below. Finally, the base 22 may include handles such as those shown at 32 in FIGS. 2A and 2B used to carry and transport the bottom portion 20 of the container and the fully assembled container 10.

The top portion 40 of the container includes a rectangular cavity 42 formed in the lower surface 44 such that, when the top portion 40 of the container is fully assembled, the pedestal 24 with the corpse resting thereon is inserted within the cavity 42 and so that the cavities 28, extending through the base 22 in the bottom portion 20, terminate within the cavity 42.

The top portion 40 of the container 10 also includes a flange 46 extending from the lower surface 44 which surrounds the perimeter of cavity 42. The flange 46 is disposed such that, when the container 10 is fully assembled, the flange 46 is inserted within the channel 26 in the bottom portion 20 of the container.

The container 10, which is only one of many configurations which can be used with the present invention, is utilized in the manner described below.

A corpse, within a relatively short period after death and preferably within 48 hours thereof, is delivered to a facility for preparation for storage.

In some cases, it may be desirable to perform cosmetic functions on the corpse to improve the appearance thereof. It is also possible that the corpse may first be embalmed for display at a post-death service. However, embalming or cosmetic treatment of the corpse is not necessary for the purposes of the present invention, and in many cases, it will be preferable to curtail or even forego such procedures to minimize expenses.

In any event, after delivery to the preparation facility, the corpse is dressed in the clothing in which it will be preserved and placed on the pedestal 24. Any final cosmetic procedures are then quickly performed.

Before assembling the top portion 40 and the bottom portion 20 of the container together, the channel 26 within the base 22 of the bottom portion, is filled with an epoxy or another adhesive which preferably dries quickly and forms a permanent bond. The top portion 40 of the container is then fitted into place over the corpse and onto the bottom portion 20 such that an air-tight, permanent bond is formed with the flange 46 in the channel 26 in the bottom portion 20 of the container.

To prevent excess stress from being placed upon the adhesive, a plurality of fasteners (not shown) may be used to mechanically secure the top portion 40 of the container to the bottom portion 20. Such fasteners would be used at either end of the container and secured to both the top portion 40 and the bottom portion 20 thereby removing the stress from the adhesive, especially during the curing period.

As previously described, one of the biological processes which contribute to decomposition of a corpse is oxidation. Consequently, the next step in the preparation of the corpse for storage is an atmospheric exchange. Specifically, a nozzle, which is coupled at one end to a supply of inert gas such as helium or argon is inserted into one of the cavities 28. The inert gas is then forced into the inner cavity 42 within the container 10 displacing the atmospheric contents therein, particularly the oxygen, through the remaining cavity 28 which acts as an exhaust valve.

After a sufficient amount of inert gas is forced into the cavity 42 to displace all of the original atmospheric contents, the cavity 28, used as the exhaust valve, is sealed with an appropriate sealer such as, for example, a threaded or tapered plug (not shown) comprised of the same material as the container 10. If a tapered plug is used, it is preferable that cavity 28 be tapered at its extremity so that the plug is completely inserted within the cavity where it reaches the point where it may be inserted no further. It is also preferable to use an epoxy or other sealant with the plug (whether tapered or threaded) to insure that an air-tight, permanent bond is maintained.

After the exhaust cavity is sealed, the cavity 42 within the container 10 should continue to be filled with the inert gas so that the pressure within the cavity slightly exceeds that outside the container 10. The nozzle is then quickly removed from the cavity 28 and the cavity is expeditiously sealed with another plug in the manner described above. Filling the cavity 42 to a pressure that exceeds the atmospheric pressure outside the container 10 insures that, during the time required to remove the nozzle and seal the cavity, the pressure differential will force the inert gas out of the cavity 42 preventing the outside atmosphere and, in particular, oxygen from re-entering.

To deactivate enzymes, which normally break down and contribute to the decomposition of the corpse, a relatively mild heat treatment is used in the next step. In the preferred embodiment of the present invention, the container 10 with the corpse resting on the base 22 in an inert atmosphere is next subjected to a microwave heat treatment sufficient to deactivate the proteolytic and lypolytic enzymes. A microwave heat treatment sufficient to heat the corpse to a temperature of approximately 160° F. for approximately one-half hour is sufficient for this purpose. The microwave treatment would also destroy microorganisms and insects present at or near the surface of the corpse. However, such a mild heat treatment would not result in discoloration or any other noticeable cosmetic reaction nor would it cause any material chemical reaction to take place within the corpse. In addition to microwave, other methods of heating the corpse may be used in the present invention.

In most situations, however, the heat treatment will not be sufficient to destroy microorganisms and putrefactive bacteria within the body. Consequently, the next and last step in the process is to irradiate the container 10 with x-rays or gamma rays. More particularly, the container 10 is irradiated with approximately 10 MeV of x-ray radiation (or 5.6 megarads of gamma rays) which will effectively kill all such bacteria and microorganisms within the corpse.

It should be noted that the steps of heating or irradiating need not be performed immediately and, in fact, either or both may be delayed for substantial periods of time by refrigerating the corpse. Moreover, in many situations the step of heating the corpse may be omitted if, for example, the corpse is encased in the container and irradiated within a short time (e.g. within 12 hours) after death.

It should also be noted that the order in which the steps of the present invention are performed is not fixed to the sequence described above and that other sequences may be used with the same effect. However, it is preferable to encase the corpse first so that, after heating and irradiation, further contamination by bacteria and microorganisms is prevented.

Also, it may not be necessary to perform the step of atmospheric exchange if, for example, the other steps in the present invention are performed quickly and depending upon the climatic condition under which the corpse will be ultimately stored.

From the foregoing description of the present invention, it can be appreciated that the container 10 used to store the body can be comprised of different materials, shapes or configurations. For example, the container could be shaped in the form of a traditional casket or as an insert which will allow the container with the corpse therein to be inserted within a traditional casket. Additionally, it can be appreciated that the present invention can be used to preserve the corpses of other forms of animal life.

While the invention has been described in its preferred embodiment, it is to be understood that the words that have been used are words of description rather than limitation and that changes may be made within the purview of the appended claims without departing from the true scope and spirit of the invention in it broader aspects.

I claim:

1. A method of preserving anatomical specimens including:
   A. encasing the specimen in an air-tight container;
   B. exchanging the atmospheric contents within the container surrounding the specimen with an inert gas; and
   C. irradiating the specimen to destroy bacteria and microorganisms.

2. The method of claim 1 further including the step of heating the container with the specimen therein to deactivate enzymes.

3. The method of claim 2 wherein the step of heating the specimen is comprised of heating the specimen to a temperature of approximately 160° F. for approximately one-half hour.

4. The method of claim 3 wherein the heating is performed with microwave apparatus.

5. The method of claim 1 wherein the step of irradiating the specimen is comprised of subjecting the container with the specimen therein to x-ray radiation of approximately 10 MeV.

6. The method of claim 1 wherein the step of irradiating the specimen is comprised of subjecting the container with the specimen therein to gamma ray radiation of approximately 5.6 megarads.

7. The method of claim 1 wherein the container used to encase the specimen is comprised of a bottom portion on which the specimen is placed and a top portion, adapted to be permanently encased therein.

8. The method of claim 7 wherein the container includes at least two orifices for exchanging the atmospheric contents within the container with an inert gas.

9. The method of claim 1 wherein the container used to encase the specimen is comprised of a plastic polymer.

10. A method of storing and preserving anatomical specimens comprising the steps of:
    A. encasing the specimen in a plastic polymer container;
    B. replacing the atmospheric contents within the container with an inert gas;
    C. sealing the container such that it becomes air-tight;
    D. heating the specimen;
    E. irradiating the specimen.

11. The method of claim 10 wherein the specimen is heated to a temperature of approximately 160° F. for a period of approximately one-half hour.

12. The method of claim 10 wherein the step of irradiating the specimen comprises subjecting the specimen within the container to x-ray radiation of approximately 10 MeV.

13. The method of claim 10 wherein the step of irradiating the specimen comprises subjecting the specimen, within the container, to approximately 5.6 megarads of gamma ray radiation.

* * * * *